US006999551B2

(12) United States Patent
Bressel et al.

(10) Patent No.: US 6,999,551 B2
(45) Date of Patent: Feb. 14, 2006

(54) METHOD FOR DIAPHRAGM REGULATION IN A COMPUTED TOMOGRAPHY APPARATUS, AND COMPUTED TOMOGRAPHY APPARATUS WITH DIAPHRAGM REGULATION

(75) Inventors: Wolfgang Bressel, Erlangen-Buckenhof (DE); Heinrich Wallschläger, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 14 days.

(21) Appl. No.: 10/441,766

(22) Filed: May 20, 2003

(65) Prior Publication Data

US 2003/0219092 A1    Nov. 27, 2003

(30) Foreign Application Priority Data

May 21, 2002   (DE)   ................................ 102 22 397

(51) Int. Cl.
    *G21K 1/02*    (2006.01)
(52) U.S. Cl. .......................................... 378/16; 378/151
(58) Field of Classification Search .................... 378/4, 378/16, 145, 151, 207, 8, 19, 5, 14, 20, 17, 378/205, 147–148, 108
See application file for complete search history.

(56) References Cited

U.S. PATENT DOCUMENTS

| | | | |
|---|---|---|---|
| 3,755,672 A * | 8/1973 | Edholm et al. | 378/158 |
| 5,287,396 A | 2/1994 | Stegebuis | |
| 5,299,250 A * | 3/1994 | Styrnol et al. | 378/19 |
| 6,055,295 A * | 4/2000 | Murthy et al. | 378/151 |
| 6,243,438 B1 * | 6/2001 | Nahaliel et al. | 378/19 |
| 6,320,929 B1 * | 11/2001 | Von Der Haar | 378/4 |
| 6,445,761 B1 * | 9/2002 | Miyazaki et al. | 378/8 |
| 6,507,642 B1 * | 1/2003 | Fujishige et al. | 378/151 |

OTHER PUBLICATIONS

"Bildgebende Systeme für die medizinische Diagnostik," Morneburg, Ed., 3rd ed. (1995) pp. 109-151.

* cited by examiner

*Primary Examiner*—David V. Bruce
*Assistant Examiner*—Hoon Song
(74) *Attorney, Agent, or Firm*—Schiff Hardin LLP

(57) ABSTRACT

In a method for diaphragm regulation in a computed tomography system and a computed tomography system with diaphragm regulation and a multi-line detector, the image detector signals are utilized for generating a setting signal for the diaphragm.

38 Claims, 3 Drawing Sheets

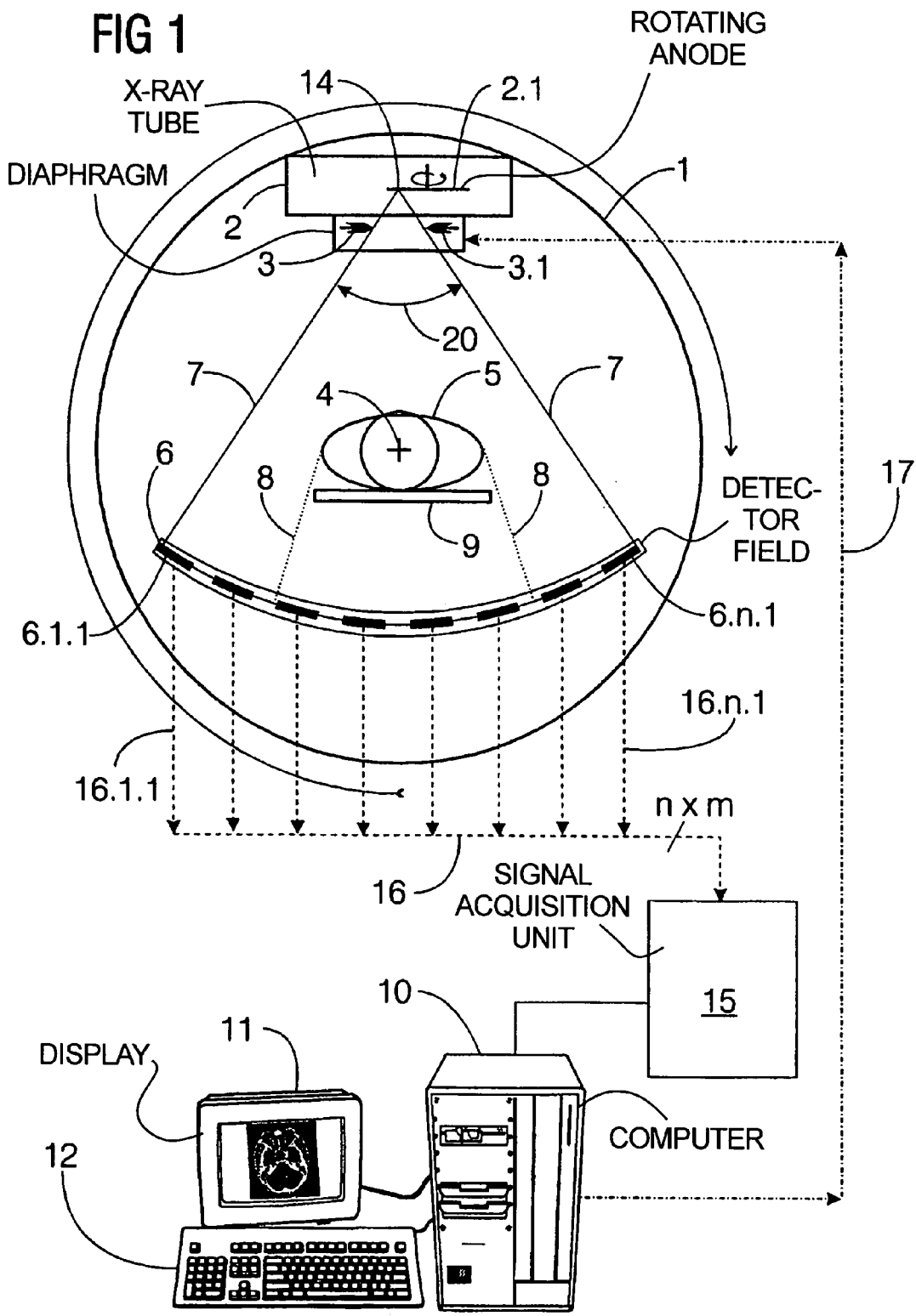

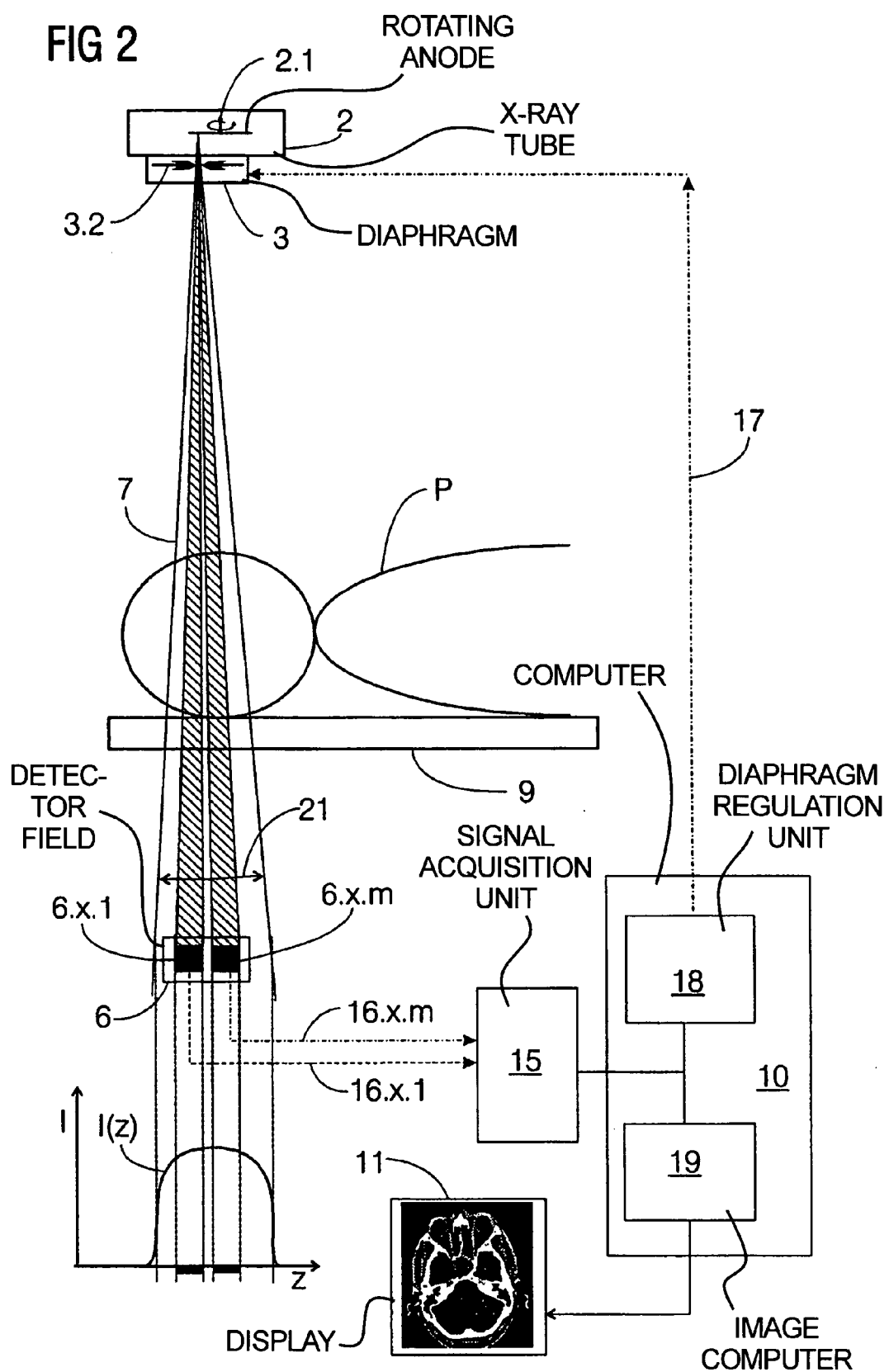

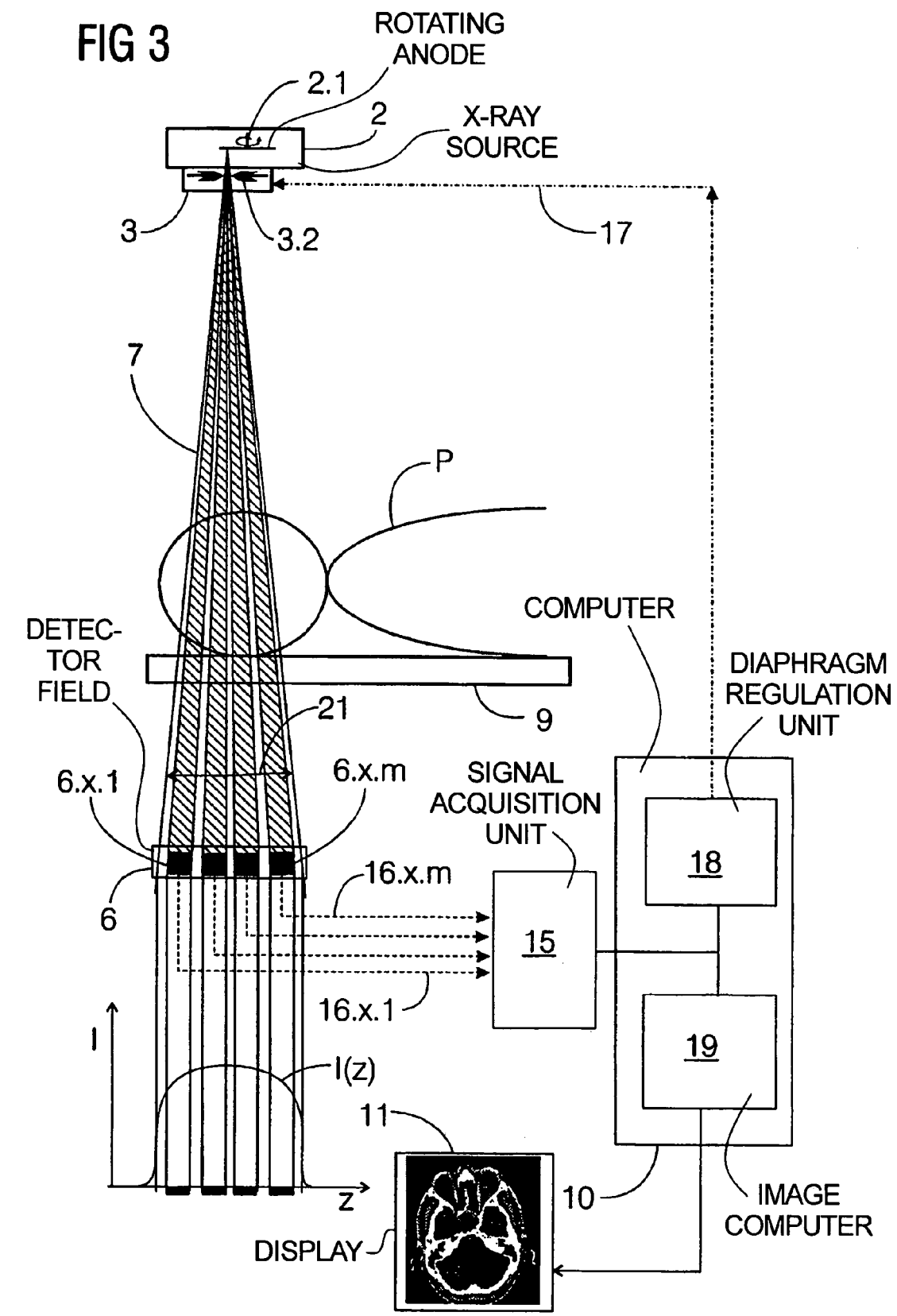

METHOD FOR DIAPHRAGM REGULATION IN A COMPUTED TOMOGRAPHY APPARATUS, AND COMPUTED TOMOGRAPHY APPARATUS WITH DIAPHRAGM REGULATION

BACKGROUND OF THE INVENTION

1. Field of the Invention

The invention is directed to a method for diaphragm regulation in a computed tomography apparatus.

2. Description of the Prior Art

Computed tomography systems are known that have a measuring unit composed of a radiation source and a radiation receiver and a subject carrier arranged therebetween on which an examination subject is located. The radiation source and detector rotate another around a system axis, and, with the assistance of a computer system, the radiation transmitted to the radiation receiver is measured with respect to its intensity distribution in a detector field, which includes at least one line of radiation-sensitive image detectors arranged around the focus of the radiation source, in order to calculate the attenuation distribution in at least one plane of the examination subject. The subject occludes only a part of the fan-shaped beam from the radiation receiver. A diaphragm is disposed between the focus of the x-ray source and the subject, which is adjustable by a control arrangement to shape the radiation beam.

German OS 199 05 974 A1 and U.S. Pat. No. 5,287,396 disclose conventional X-ray devices that undertake an image evaluation, for example with contour recognition, for the diaphragm adjustment.

Computed tomography systems generate tomographic exposures of an examination subject, usually a patient, using tissue-penetrating radiation. The publication "Bildgebende Systeme für die medizinische Diagnostik," Heinz Morneburg, Editor, $3^{rd}$ Edition, particularly Chapter 5, "Prinzipien der Röntgen-Computertomographie", describes the basic principles of computed tomography, particularly X-ray computed tomography.

In systems referred to as fan-beam devices the X-ray beam emanating from the radiation source is limited by the adjustable diaphragm to form a fan beam which penetrates the examination subject. Subsequently, the attenuation of the X-rays is measured at the other side of the patient in a detector field curved around the focus of the radiation source. The entire measuring unit composed of the radiation source and the radiation receiver rotates around the subject. The rotational axis is referred to as the system axis. The attenuation properties of the transirradiated subject in one or more planes are calculated on the basis of the measured attenuation of the radiation in the individual sectors and from different rotational angles of the measuring unit and are reproduced on a display or image carrier. Any ionizing radiation can be employed as the radiation, but X-rays generated by an X-ray tube with a rotating anode usually represents the most commonly employed radiation.

In order to achieve tomograms with good quality, it is necessary to obtain a good illumination of the detector field and retain it as much as possible during the entire exposure activity. Since the radiation stress on the patient should be as low as possible in the production of the tomographic exposure, efforts are made to limit the fan-shaped ray beam to be as narrow as possible, using an adjustable diaphragm. Such a diaphragm is disclosed, for example, in German OS 199 05 974.

Due to the narrow diaphragm setting, however, slight movements or boundary conditions that are change in some other way such as, for example, the thermal focus movement or tilting of the measuring unit (gantry tilting), frequently have a detrimental influence on the quality of the irradiation.

German Patent 42 07 006 discloses an X-ray computed tomography apparatus that has regulation of the diaphragm for these reasons. This diaphragm regulation is obtained by attaching specific position detectors at the edges of the detector field, these being struck by the fan-shaped beam and, by measuring the intensity distribution of the radiation on the specific position detectors, a migration of the beam is recognized as a consequence of a change of the focus position in the X-ray tube, so that a re-adjustment of the diaphragm can ensue immediately in order to again achieve a good irradiation of the detector field.

A disadvantage of this device and method for diaphragm adjustment is that additional, specific position detectors are needed, that are relatively complicated since the detectors must be able to identify the spatial distribution of the radiation.

SUMMARY OF THE INVENTION

An object of the present invention is to provide a method for diaphragm regulation in a computed tomograph that does not require the aforementioned position detectors.

A further object of the invention is to provide a computed tomography apparatus with diaphragm regulation without the use of the aforementioned positions detectors.

The above objects are achieved in accordance with the invention in a computed tomography apparatus having a diaphragm and a multi-line detector, and a method for operating such a computed tomography apparatus, wherein image detector information is obtained from the image detector and used to regulate the diaphragm.

The inventive method and computed tomography apparatus are based on the recognition that, with a multi-row or multi-line detector field, the detection signals (image detector information) which are already present for image generation can be used to identify the quality of the irradiation and shifts in the irradiation as may occur, so that a control circuit for the diaphragm regulation can be formed using these signals.

In an embodiment of the invention computed tomography apparatus has a measuring unit composed of a radiation source and a radiation detector and a subject carrier arranged therebetween on which an examination subject is located, the measuring unit and the radiation source being rotatable around a system axis. With a computer system, the fan beam radiation at the radiation receiver is measured with respect to its intensity distribution in a detector field, which contains at least two parallel lines of radiation-sensitive image detectors aligned to the focus of the radiation source. The computer calculates the attenuation distribution in at least one plane of the examination subject. At least a portion of the image detector information utilized for the calculation of the attenuation distribution is used for regulating the diaphragm position (i.e. the position or spacing of the diaphragm plates). The image detector information can be evaluated line-by-line.

By comparing the detected intensities from identical sectors of different detector rows, it is possible to identify changes in the irradiation based on the variation of intensity distributions in these sectors, and to supply a setting signal to the diaphragm so that a fast regulation of the diaphragm is achieved.

Preferably, only detector information that arise from non-occluded regions of the detector field is employed for the regulation (setting signal), so that the influence of the subject can be eliminated, since the subjects may have a non-uniform distribution of attenuation coefficients. When examining a human or animal patient as the subject, It is always the case that only the detector information from non-occluded regions should be used.

The occlusion-free regions can be identified, for example, by an upward transgression of a threshold of the detected radiation intensity since, of course, the radiation intensity is reduced in the occluded region. It can be advantageous to set a safety margin between occlusion-free and occluded regions, with detected radiation in this safety margin also being excluded from employment for regulating the diaphragm.

In accordance with the invention, a difference quantity between the (at least) two lines of image detectors in the same angular channel segment can be employed as a regulating variable, the difference quantity preferably being derived from the averages of a group of detectors. For excluding anomalies, at least one lowest and at least one highest discrete value per group can be discarded. Disturbances in the measurement can be suppressed by this measure.

When the computed tomography apparatus has an X-ray tube with a rotating anode as the x-ray source, or when some other effects can lead to rapidly fluctuating intensities of the radiation over time, then all measured quantities are averaged over a time span that allows these temporal fluctuations to be compensated.

Since the subject itself usually is centrally located over the detector field and it is certain that no occlusion-free regions are present in this area, only predefined, preferably edge-proximate angular channel segments and their image detector information are used for regulating the diaphragm position.

In a further embodiment only measurements that are acquired at a specific rotational angle of the measuring unit are employed for regulating the diaphragm position. Centrifugal and gravitational force acting on the rotating anode thus do not add or subtract in the determination of the setting signal.

It is known that an adjustment of the diaphragm is especially needed when the measuring unit moves, i.e. rotates around the system axis. In this case, centrifugal forces occur and will be dependent on the rotational speed, among other things. During standstill of the measuring unit, essentially only thermally dependent changes need to be compensated. In an embodiment of the invention, therefore, the frequency of the evaluation of the measured data for regulating the diaphragm position is constant given a non-rotating measuring unit, and the measured data evaluation occurs more frequently given a rotating measuring unit. For example, the frequency with w hitch the evaluation is undertaken can be set directly proportional to the rotational speed. There is also the possibility of adapting only the increase itself proportionally to the rotational speed, starting from a base evaluation frequency (rate).

When more than two lines of image detectors are employed, it can be advantageous, for reducing the measurement and calculating outlay, to use only the measurements of image detectors of suitable lines for regulating the diaphragm position, preferably the first and last lines.

It is also possible, given the use of more than two lines of image detectors to employ measurements from identical angular channel segments of a number of lines for regulation of the diaphragm position, in order to determine an intensity curve of the radiation over these lines, and to employ the position of the maximum of the intensity curve as a regulating variable for the diaphragm positioning.

If an additional improvement of the diaphragm regulation is desired by generating a redundancy, then the known, specific position detectors can be additionally separately employed. These position detectors can be installed at the radiator was well as at the receiver. The additional position detectors can be employed for the diaphragm regulation when no occlusion-free image detector signal is available.

In such an embodiment, two overlapping control circuits can be employed. A first control circuit receives signals from the image detectors as a regulating variable and a second control circuit receives signals from the specific position detectors as a regulating variable. The control circuits preferably are weighted corresponding to the quality and/or dependability of the regulating variable, so that an overall optimization of the diaphragm setting is achieved.

In addition to the optional omission of specific position detectors, an advantageous method and apparatus is that an adjustable diaphragm at the detector can be foregone due to the extremely precise adjustment of the diaphragm at the radiation source. As a result, an improved dose utilization can be produced, so that the overall radiation stress on an examined patient is reduced.

Since the regulating signals are always available for the control of the diaphragm, it is also possible to use these in the preparation of calibration tables with which the computed tomography is calibrated, with only exposures wherein the dose profile is accurately positioned in the direction of the system axis being evaluated. As a result, qualitatively better calibration tables that have a higher accuracy are produced, thereby minimizing or eliminating maladjustments of the diaphragm.

DESCRIPTION OF THE DRAWINGS

FIG. 1 is a schematic illustration of an X-ray computed tomography in a cross-section perpendicular to the symmetry axis, including a computer unit.

FIG. 2 shows an X-ray computed tomography apparatus in longitudinal section along the system axis with two image detector lines.

FIG. 3 shows an X-ray computed tomography apparatus in longitudinal section along the system axis with four image detector lines.

DESCRIPTION OF THE PREFERRED EMBODIMENTS

FIG. 1 is a schematic illustration of an embodiment of a computed tomography system in the form of an X-ray computed tomography system shown in cross-section. The section is perpendicular to the system axis 4 around which the measuring unit or gantry of the computed tomography system rotates for the production of tomograms. The measuring unit is composed of an X-ray tube 2 that is equipped with a rotating anode 2.1 for generating X-rays. The X-ray beam from the rotating anode 2.1 is limited and set with a diaphragm adjustment device 3 with an integrated diaphragm 3.1 in the transverse direction and a diaphragm 3.2 in the longitudinal direction. A detector is located under the X-ray tube 2, the detector having a detector field 6 that is formed by a number of a plurality of detectors 6.1.1 through 6.$n.m$ in m rows and m columns. Due to the sectional illustration, however, the rows arranged behind one another can not be directly seen in FIG. 1; but only the first row with the detectors 6.1.1 through 6.$n$.1 is shown.

A patient bed of a subject table 9, on which a patient 5 (subject) to be examined is schematically shown with torso and head, is situated between the X-ray tube 2 and the detector field or radiation receiver 6. The patient is located in a beam path of a fan-shaped X-ray beam 7 and occludes the detector field from the X-ray tube 2 in the segment that is shown by the broken-line course 8 of the radiation. Beyond the segment limited by the rays 8, the X-ray beam proceeds occlusion-free to the detector field.

In the detector field, the measured radiation signal intensity values are supplied to a signal acquisition unit 15 via signal lines 16.1.1 through 16.$n$.1 and the collecting line 16 from m rows and n columns of image detectors. Of course, the other detector rows that are not visible here are also evaluated by the signal acquisition unit 15 and are forwarded in digital form to a computer unit 10 in order to be available for the image formation.

As more specifically shown in FIGS. 3 and 4, in accordance with the invention, the existing signals of the detector field 6, are used not only for the image preparation in an image computer 19 but also for determining the illumination of the detector field by the fan-shaped X-ray beam in a diaphragm regulation unit 18. Irregularities and modifications of the irradiation of the detector field 6 are identified in the diaphragm regulation unit 18, which forwards signals via a control line 17 to the diaphragm adjustment device 3, so that the appropriate diaphragm adjustment can be undertaken to again obtain a uniform irradiation of the detector field.

In addition to the inventive use, the measured detector signals are employed, as is conventional, for producing tomograms that can be subsequently presented on a display 11, controlled by the keyboard 12.

The fan is set in the direction of the system axis 4, since care must be exercised to obtain an especially narrow radiation field. The width of this radiation field along the system axis is a significant factor for defining the dose stress applied to the patient in the production of the CT exposures. FIGS. 2 and 3 therefore again show a section through an inventive X-ray CT system in the longitudinal direction, FIG. 2 shows a detector field 6 that is fashioned with two rows, whereas FIG. 3 shows a detector field fashioned with four rows.

FIG. 2 includes position detectors 20 in the detector field, that respectively emit detector outputs identifying the position of the diaphragm 3.

The intensity distribution I(z) is shown in a coordinate system under the detector 6 in spatial dependence on the detectors situated thereabove. The z-axis of the coordinate system corresponds to the system axis 4 of the computed tomography system, with the intensity I of the X-rays entered on the ordinate. It can be seen in the illustrated embodiment that the X-ray are slightly shifted toward the right with respect to the maximum and limits at the point in time of the exposure. Consequently, a different intensity of the X-rays is also measured at the detectors of a different row and identical line. This difference signal can be obtained from the information normally employed for producing a tomogram, so that a corresponding modification of the diaphragm that subsequently leads to a restoration of a uniform irradiation of the detector field can be controlled via a control circuit.

The same applies to the computed tomography system shown in FIG. 3, having a four-line detector field 6.1.1 through 6.$n$.4, but only the outer row of detectors can be utilized according to the above-described method for setting the detector field irradiation or the diaphragm regulation and their difference signal is identified and can then serve as a regulating variable for setting the diaphragm. In the simplest case, for example, only the detectors 6.1.1, 6.1.$m$, 6.$n$.1, and 6.$n$.$m$ can be utilized for the diaphragm control, and a rotation of the diaphragm aperture around a vertical axis also can be regulated in addition to the width and length adjustment, if this is necessary.

With more than three detector lines, the measured values of the individual rows also can be utilized in order to produce an intensity profile in the Z-direction by means of an approximation calculation or direct solution of an equation system. The position of the calculated maximum of this intensity distribution and its deviation from the actual middle of the detector lines thus can be employed as the regulating variable for setting the diaphragm control. When the position of the maximum at both sides of the detector field is determined, then a rotating of the ray fan perpendicular to the system axis can be detected as a result, and compensated as warranted.

In the schematic illustration of FIGS. 1 through 3, image detectors and their spacings from one another are shown relatively large for clarity. Typical fan angles are 50°. The expanse of the detector in the z-direction typically amounts to approximately 20 mm.

As a result of the inventive design of a computed tomography system, particularly the diaphragm regulation, and the application of the described method for diaphragm regulation, it is possible to employ the detector signals, that conventionally served only for image generation, in a control circuit for the diaphragm control of the X-ray tube, so that a very efficient and economical diaphragm regulation is possible.

It should be noted that the examples of a computed tomography system shown herein merely represent a preferred embodiment of the invention. Such a diaphragm control is likewise possible for gamma radiators, beta radiators, other ionizing radiation, or even in ultrasound tomography systems.

Although modifications and changes may be suggested by those skilled in the art, it is the intention of the inventors to embody within the patent warranted hereon all changes and modifications as reasonably and properly come within the scope of their contribution to the art.

We claim as our intention:

1. A method for operating a computed tomography apparatus comprising the steps of:
    disposing an examination subject between an x-ray source and a multi-line radiation detector having at least two parallel lines of image detectors;
    emitting x-rays from said x-ray source and limiting said x-rays with a diaphragm to form a fan-shaped x-ray beam;
    irradiating said examination subject with said fan-shaped x-ray beam while rotating said x-ray source and said radiation detector around a system axis, said examination subject occluding only a portion of said fan-shaped beam from said radiation detector;
    obtaining image information from said radiation detector dependent on said fan-shaped beam incident thereon;
    in a computer system, calculating an intensity distribution from said image information;
    identifying regions of said radiation detector that are not occluded by said examination subject by comparing said intensity distribution to a threshold and identifying said regions where said threshold is exceeded; and employing only image information from said regions of said radiation detector that are not occluded by said examination subject for regulating a position of said diaphragm.

2. A method as claimed in claim 1 comprising identifying a difference quantity between two corresponding channels of at least two lines of said radiation detector in a same angular channel segment as a regulating variable for regulating said diaphragm.

3. A method as claimed in claim 2 comprising identifying said difference quantity from average output signals respectively from a group of detectors in said at least two lines.

4. A method as claimed in claim 3 wherein said group of detectors generates a lowest discrete output signal value and a highest discrete output signal value, and comprising the step of discarding said lowest and highest discrete output signal values in forming said average.

5. A method as claimed in claim 1 comprising averaging all output signals from said radiation detector over a time span for compensating for temporal fluctuations in said output signals.

6. A method as claimed in claim 1 wherein said at least two detector lines have prescribed angular channel segments disposed at an edge of said radiation detector, and comprising the step of employing only image information from said prescribed angular channel segments for regulating said diaphragm.

7. A method as claimed in claim 1 comprising employing only output signals from said radiation receiver obtained at a predetermined rotational angle of said x-ray fan beam relative to said system axis for regulating said diaphragm.

8. A method as claimed in claim 7 wherein said x-ray source and said radiation detector form a measuring unit, and selecting said rotational angle as an angle where forces acting on said measuring unit during rotation substantially compensate each other.

9. A method as claimed in claim 1 comprising evaluating said image information for regulating said diaphragm at a constant frequency given non-rotation of said x-ray source and said radiation detector.

10. A method as claimed in claim 1 comprising evaluating said image information for regulating said diaphragm at a frequency proportional to a rotational speed of said x-ray source and said radiation detector around said system axis.

11. A method as claimed in claim 1 wherein said radiation detector comprises multiple lines and image detectors, including said at least two parallel lines and image detectors, and employing image information from said multiple lines of image detectors for regulating said diaphragm.

12. A method as claimed in claim 10 wherein said multiple lines of image detectors include a first line of image detectors and a last line of image detectors, and employing image information from said first line of image detectors and said last line of image detectors for regulating said diaphragm.

13. A method for operating a computed tomography apparatus comprising the steps of:
 disposing an examination subject between an x-ray source and a multi-line radiation detector having multiple parallel lines of image detectors;
 emitting x-rays from said x-ray source and limiting said x-rays with a diaphragm to form a fan-shaped x-ray beam;
 irradiating said examination subject with said fan-shaped x-ray beam while rotating said x-ray source and said radiation detector around a system axis, said examination subject occluding only a portion of said fan-shaped beam from said radiation detector;
 obtaining image information from said radiation detector dependent on said fan-shaped beam incident thereon; and
 employing image information from identical channel segments of a plurality of said multiple lines for regulating said diaphragm, by determining an intensity curve of said x-rays over said multiple lines and identifying a maximum of an intensity curve over said multiple lines and employing said maximum as a regulating variable for regulating said diaphragm.

14. A method as claimed in claim 1 comprising providing position detectors for emitting detector outputs identifying said position of said diaphragm.

15. A method as claimed in claim 14 comprising employing said detector outputs for regulating said diaphragm if no image information is available from a region of said radiation detector that is not occluded by said examination subject.

16. A method as claimed in claim 14 comprising generating a first control signal for regulating said diaphragm from said image information and generating a second control signal for regulating said diaphragm from said detector outputs.

17. A method as claimed in claim 16 comprising selectively weighting said first and second control signals dependent on a characteristic selected from quality and reliability of said first and second control signals.

18. A method as claimed in claim 1 comprising generating a calibration table from said image information for regulating said diaphragm, and using only image information for generating said calibration table wherein said detector field is uniformly irradiated.

19. A method as claimed in claim 18 comprising employing only image information for generating said calibration table wherein said detector field is uniformly irradiated along a direction of said system axis.

20. A computed tomography apparatus comprising:
 a measuring unit rotatable around a system axis having a radiation source which emits x-rays, an adjustable diaphragm disposed in a path of said x-rays for limiting said x-rays to generate a fan shaped x-ray beam, and a radiation detector on which said fan-shaped x-ray beam is incident, having a detector field composed of at least two parallel lines of image detectors which generate output signals containing image information dependent on x-rays incident thereon;
 a computer supplied with said output signals for calculating an attenuation distribution of said x-rays in at least one plane defined by said at least two parallel lines of image detectors; and
 a control unit supplied with said image information, said control unit identifying regions of said radiation detector that are not occluded by said examination subject by comparing said intensity distribution to a threshold and identifying said regions where said threshold is exceeded and control unit employing only image information from regions of said radiation detector which are not occluded by said examination subject for regulating said diaphragm for regulating a position of said diaphragm.

21. A computed tomography apparatus as claimed in claim 20 wherein said control unit identifies a difference quantity between two corresponding channels of at least two lines of said radiation detector in a same angular channel segment as a regulating variable for regulating said diaphragm.

22. A computed tomography apparatus as claimed in claim 21 wherein said control unit identifies said difference quantity from average output signals respectively from a group of detectors in said at least two lines.

23. A computed tomography apparatus as claimed in claim 22 wherein said group of detectors generates a lowest discrete output signal value and a highest discrete output signal value, and wherein said control unit discards said lowest and highest discrete output signal values in forming said average.

24. A computed tomography apparatus as claimed in claim 20 wherein said control unit averages all output signals from said radiation detector over a time span for compensating for temporal fluctuations in said output signals.

25. A computed tomography apparatus as claimed in claim 20 wherein said at least two detector lines have prescribed angular channel segments disposed at an edge of said radiation detector, and wherein said control unit employs only image information from said prescribed angular channel segments for regulating said diaphragm.

26. A computed tomography apparatus as claimed in claim 20 wherein said control unit employs only output signals from said radiation receiver obtained at a predetermined rotational angle of said x-ray fan beam relative to said system axis for regulating said diaphragm.

27. A computed tomography apparatus as claimed in claim 26 wherein said control unit selects said rotational angle as an angle where forces acting on said measuring unit during rotation substantially compensate each other.

28. A computed tomography apparatus as claimed in claim 20 wherein said control unit evaluates said image information for regulating said diaphragm at a constant frequency given non-rotation of said x-ray source and said radiation detector.

29. A computed tomography apparatus as claimed in claim 20 wherein said control unit evaluates said image information for regulating said diaphragm at a frequency proportional to a rotational speed of said x-ray source and said radiation detector around said system axis.

30. A computed tomography apparatus as claimed in claim 20 wherein said radiation detector comprises multiple lines and image detectors, including said at least two parallel lines and image detectors, and wherein said control unit employs image information from said multiple lines of image detectors for regulating said diaphragm.

31. A computed tomography apparatus as claimed in claim 26 wherein said multiple lines of image detectors include a first line of image detectors and a last line of image detectors, and wherein said control unit employs image information from said first line of image detectors and said last line of image detectors for regulating said diaphragm.

32. A computed tomography apparatus as claimed in claim 27 wherein said control unit employs image information from identical channel segments of a plurality of said multiple lines for regulating said diaphragm, by determining an intensity curve of said x-rays over said multiple lines, and identifying a maximum of an intensity curve over said multiple lines, and employs said maximum as a regulating variable for regulating said diaphragm.

33. A computed tomography apparatus as claimed in claim 20 comprising position detectors for emitting detector outputs to said control unit identifying said position of said diaphragm.

34. A computed tomography apparatus as claimed in claim 33 wherein said control unit employs said detector outputs for regulating said diaphragm if no image information is available from a region of said radiation detector that is not occluded by said examination subject.

35. A computed tomography apparatus as claimed in claim 33 wherein said control unit generates a first control signal for regulating said diaphragm from said image information and generates a second control signal for reguiating said diaphragm from said detector outputs.

36. A computed tomography apparatus as claimed in claim 35 wherein said control unit selectively weights said first and second control signals dependent on a characteristic selected from qualify and reliability of said first and second control signals.

37. A computed tomography apparatus as claimed in claim 20 comprising a memory, accessible by said control unit, containing a calibration table separated from said image information using only image information wherein said detector field is uniformly irradiated, said control unit reguiating said diaphragm using said image information in said calibration table.

38. A computed tomography apparatus as claimed in claim 37 wherein said calibration table contains only image information wherein said detector field is uniformly irradiated along a direction of said system axis.

* * * * *